US006682916B2

(12) United States Patent
Taoka et al.

(10) Patent No.: US 6,682,916 B2
(45) Date of Patent: Jan. 27, 2004

(54) CHLOROHYDROXYACETONE DERIVATIVE AND PROCESS FOR PRODUCING OPTICALLY ACTIVE CHLOROPROPANEDIOL DERIVATIVE FROM THE SAME

(75) Inventors: Naoaki Taoka, Kobe (JP); Hironobu Maeda, Kobe (JP); Kazumi Okuro, Kobe (JP); Koichiro Toyota, Akashi (JP); Yoshihiko Yasohara, Himeji (JP)

(73) Assignee: Kaneka Corporation, Osaka (JP)

( * ) Notice: Subject to any disclaimer, the term of this patent is extended or adjusted under 35 U.S.C. 154(b) by 58 days.

(21) Appl. No.: 10/069,105

(22) PCT Filed: Jun. 22, 2001

(86) PCT No.: PCT/JP01/05363
§ 371 (c)(1), (2), (4) Date: Feb. 26, 2002

(87) PCT Pub. No.: WO02/00585
PCT Pub. Date: Jan. 3, 2002

(65) Prior Publication Data
US 2002/0160398 A1 Oct. 31, 2002

(30) Foreign Application Priority Data
Jun. 27, 2000 (JP) ........................................ 2000-192245

(51) Int. Cl.[7] .............................. F12P 7/18; C12P 1/02
(52) U.S. Cl. .................. 435/158; 435/171; 435/252.33; 435/252.8; 435/254.22
(58) Field of Search ................................. 435/158, 280, 435/911, 252.8, 252.33, 254.22, 255.4, 171

(56) References Cited

U.S. PATENT DOCUMENTS 5,266,485 A * 11/1993 Sawa et al. ................. 435/280
6,218,156 B1 * 4/2001 Yasohara et al. ........... 435/280

FOREIGN PATENT DOCUMENTS

JP 4-267883 9/1992
JP 11-103878 4/1999

OTHER PUBLICATIONS

H. Oguri et al.; Synlett, No. 12, pp. 1252–1254, 1995.

E. C. Taylor et al.; J. Am. Chem. Soc., vol. 111, No. 1, pp. 285–291, 1989.

N. Bodor et al.; J. Med. Chem.; vol. 31, No. 1, pp. 100–106, 1988.

L. V. Hijfte et al.; Tetrahedron Letters, vol. 34, No. 30, pp. 4793–4796, 1993.

D. L. Boger et al.; J. Am. Chem. Soc. vol. 114, No. 24, pp. 93218–93227, 1992.

* cited by examiner

*Primary Examiner*—Herbert J. Lilling
(74) *Attorney, Agent, or Firm*—Armstrong, Westerman & Hattori, LLP

(57) ABSTRACT

A process for efficiently preparing an optically active chloropropanediol derivative, especially (S)-1-benzyloxy-3-chloro-2-propanol, which has a high optical purity and is useful as an intermediate for medicines. The process comprises treating an inexpensive racemic chloropropanediol derivative with a nitroxyl compound and an oxidizing agent to convert it into a chlorohydroxyacetone derivative and then stereospecifically reducing the carbonyl group of the chlorohydroxyacetone derivative by the action of either a carbonyl-reducing enzyme having the ability to stereospecifically reduce the chlorohydroxyacetone derivative or an optically treated culture of a microorganism having the ability to yield the carbonyl-reducing enzyme. Thus, an optically active chloropropanediol derivative is prepared.

26 Claims, No Drawings

CHLOROHYDROXYACETONE DERIVATIVE AND PROCESS FOR PRODUCING OPTICALLY ACTIVE CHLOROPROPANEDIOL DERIVATIVE FROM THE SAME

TECHNICAL FIELD

The present invention relates to a process for preparing optically active chloropropanediol derivative which comprises treating an inexpensive (RS)-chloropropanediol derivative with a nitroxyl compound in the presence of an oxidant to convert to an chlorohydroxyacetone derivative, and stereospecifically reducing the chlorohydroxyacetone derivative under an enzyme source having an activity which allow an chlorohydroxy acetone derivative to be reduced, and an important intermediate thereof. An optically active chloropropanediol derivative, especially (S)-3-benzyloxy-1-chloro-2-propanol is useful compound as an intermediate of a medicine.

BACKGROUND ART

As the process for preparing chlorohydroxyacetone derivative, for example, the process for oxidizing 1-benzoyloxy-3-chloro-2-propanol with DCC (Journal of Medicinal Chemistry, (20), 5, 1997) is known. However, such process has problems of using harmful heavy metals and of low yield.

As the reduction process of chlorohydroxyacetone with, for example, a microorganism, the following processes are known. (1) A process for stereoselective reduction of 1-acetyloxy-3-chloro-2-propanone with an microorganism (JP-A-11-103878), and (2) a process for R selective reduction of 1-chloro-3-(p-acetoamidephenoxy)-2-propanone with a microorganism (JP-A-02-295970). However, these processes have a problem in stereoselectivity, productivity or the like.

As mentioned above, these processes have a problem to be improved as an industrial preparation process.

As a result of intense studies for the purpose of preparing optically active chloropropanediol derivatives, especially (S)-1-benzyloxy-3-chloro-2-propanol effectively in a high optical purity, a process for preparing an optically active chloropropanediol derivative, which comprises treating inexpensive (RS)-chloropropanediol derivative with a nitroxyl compound in the presence of an oxidant to convert to an chlorohydroxyacetone derivative, and stereospecifically reducing the chlorohydroxyacetone derivative under an enzyme source having an activity which allow an chlorohydroxy acetone derivative to be reduced, and 1-benzyloxy-3-chloro-2-propanon which is one of important intermediates thereof have been found to complete the present invention.

DISCLOSURE OF INVENTION

That is to say, the present invention relates to a chlorohydroxyacetone derivative represented by the formula (1);

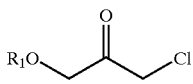

(1)

wherein $R_1$ is an aralkyl group which may be substituted with a group having 1 to 15 carbon atoms.

In the above-mentioned chlorohydroxyacetone derivative, $R_1$ is preferably benzyl group or a substituted benzyl group.

The present invention also relates to a process for preparing a chlorohydroxyacetone derivative represented by formula (3);

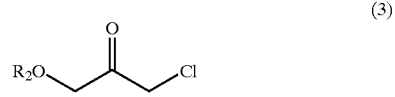

(3)

wherein $R_2$ is an alkyl group having 1 to 10 carbon atoms, an aryl group which may be substituted with a group having 1 to 15 carbon atoms, an aralkyl group which may be substituted with a group having 1 to 15 carbon atoms, an alkylsulfonyl group having 1 to 10 carbon atoms, an arylsulfonyl group which may be substituted with a group having 1 to 15 carbon atoms, an alkylcarbonyl group having 1 to 10 carbon atoms or an arylcarbonyl group which may be substituted with a group having 1 to 15 carbon atoms, which comprises allowing a chloropropanediol derivative represented by the formula (2);

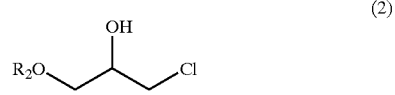

(2)

wherein $R_2$ is the same as the defined above, to react with a nitroxyl compound represented by the formula (7);

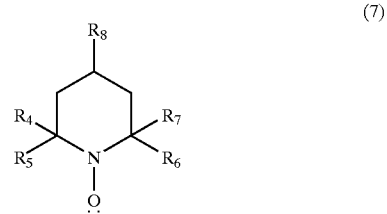

(7)

wherein each of $R_4$, $R_5$, $R_6$ and $R_7$ is an alkyl group which may be the same or different, $R_8$ is hydrogen atom or electron-releasing group, in the presence of an oxidizing agent.

Furthermore, the present invention relates to a process for preparing an optically active chloropropanediol derivative represented by the formula (4);

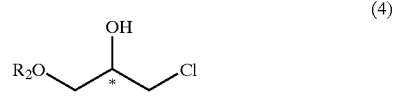

(4)

wherein $R_2$ is the same as the mentioned above, which comprises allowing chlorohydroxy acetone derivative represented by the formula (3) obtained by the above-mentioned preparing process to be stereospecifically reduced in the presence of an enzyme source having an activity to reduce it stereospecifically.

Additionally, the present invention relates to a process for preparing an optically active chloropropanediol derivative represented by the formula (6);

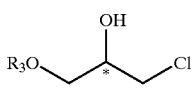

(6)

wherein $R_3$ is an alkyl group having 1 to 10 carbon atoms, an aryl group which may be substituted with a group having 1 to 15 carbon atoms, an aralkyl group which may be substituted with a group having 1 to 15 carbon atoms, an alkylsulfonyl group having 1 to 15 carbon atoms, an arylsulfonyl group which may be substituted with a group having 1 to 15 carbon atoms, which comprises allowing a chlorohydroxyacetone derivative represented by the formula (5);

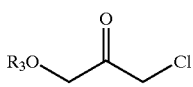

(5)

wherein $R_3$ is the same as the mentioned above, to be stereospecifically reduced in the presence of an enzyme source having an activity to reduce the chlorohydroxy acetone derivative represented by the above-mentioned formula (5) stereospecifically.

BEST MODE FOR CARRYING OUT THE INVENTION

The present invention is explained in detail below.

In the aralkyl group which may be substituted with a group having 1 to 15 carbon atoms represented by $R_1$ in the formula (1), the aralkyl group include benzyl group, phenylethyl group, phenylpropyl group, naphthylmethyl group. Among them, benzyl group is preferable. The substituent of the aralkyl group includes an alkyl group having 1 to 8 carbon atoms, an alkoxy group having 1 to 8 carbon atoms, an acyl group having 1 to 10 carbon atoms, an aliphatic amide group having 1 to 5 carbon atoms, an aliphatic ether having 1 to 5 carbon atoms, an unsaturated aliphatic ether having 1 to 5 carbon atoms, a halogen atom such as fluorine, chlorine, iodine or bromine, hydroxyl group, thiol group, nitro group, amino group, cyano group, an aryl group such as phenyl group or naphthyl group. Among them, the halogen atom such as fluorine, chlorine, iodine or bromine is preferable.

In the compounds represented by each of the formula (2) to (6), the alkyl group having 1 to 10 carbon atoms represented by $R_2$ or $R_3$ includes methyl group, ethyl group, propyl group, isopropyl group, n-butyl group, isobutyl group, sec-butyl group, t-butyl group or the like. Among them, t-butyl group is preferable. In the aryl group which may be substituted with a group having 1 to 15 carbon atoms, the aryl group includes phenyl group, naphthyl group, pyridyl group, indolinyl group or the like. Among them, phenyl group is preferable. The substituent of the aryl group includes an alkyl group having 1 to 8 carbon atoms, an alkoxy group having 1 to 8 carbon atoms, an acyl group having 1 to 10 carbon atoms, an aliphatic amide group having 1 to 5 carbon atoms, an aliphatic ether having 1 to 5 carbon atoms, an unsaturated aliphatic ether having 1 to 5 carbon atoms, a halogen atom such as fluorine, chlorine, iodine or bromine, hydroxyl group, thiol group, nitro group, amino group, cyano group, an aryl group such as phenyl group or naphthyl group. Among them, the halogen atom such as fluorine, chlorine, iodine or bromine is preferable.

The number of substituents is preferably 0 to 3. As the alkylsulfonyl group having 1 to 15 carbon atoms, methane sulfonyl group is preferable. The arylsulfonyl group which may be substituted with a group having 1 to 15 carbon atoms includes phenylsulfonyl group, p-toluenesulfonyl group or p-nitruphenylsulfonyl group. Among them, p-toluenesulfonyl group is preferable.

In the compounds represented by each of the formula (2) to (4), the alkylcarbonyl group having 1 to 10 carbon atoms represented by $R_2$ includes acetyl group, ethylcarbonyl group, propylcarbonyl group or the like. Among them, acetyl group is preferable. The arylcarbonyl group which may be substituted with a group having 1 to 15 carbon atoms includes p-bromobenzoly group or the like. Among them, benzoyl group and p-nitrobenzoly group are preferable.

It is known that, chloropropanediol derivative used as a raw material and represented by the formula (2) in the present invention, for example, (RS)-1-chloro-3-benzyloxy-2-propanol can be easily prepared by allowing epichlorohydrin to react with benzylalcohol in the presence of a Lewis acid (JP-A-02-211).

In the present invention, first chlorohydroxyaceton derivative represented by the formula (3) is prepared by oxidizing (RS)-chloropropanediol derivative represented by the formula (2) with nitroxyl compound represented by the formula (7) in the presence of an oxidant.

The oxidation process of the present invention can be carried out by adding chloropropanediol derivative and nitroxyl compound to an appropriate solvent, and by dropping and stirring oxidant thereto. The reaction condition is not limited particularly. Generally, the reaction temperature is 0 to 70° C., preferably 0 to 20° C. The reaction pH is 4 to 10, preferably 7 to 9. The concentration of substrate is 0.1 to 50% (w/v), preferably 1 to 50% (w/v). The amount of nitroxyl compound to be added is 0.001 to 1 equivalent to substrate, preferably 0.01 to 0.1 equivalent. As the reaction solvent, acetic acid, toluene or methylen chloride is used.

In the nitroxy compound represented by the formula (7), the substituent represented by $R_4$ to $R_7$ includes methyl group. As the substituent represented by $R_8$, hydrogen atom, methoxy group, benzoyloxy group, acethylamino group, oxytho group or hydroxyl group is preferable and hydrogen atom and acethylamino group is more preferable. As concrete examples of the nitroxyl compound, 2,2,6,6-tetramethylpiperidine-1-oxyl (TEMPO), 4-acethylamino-2,2,6,6-tetramethylpiperidine-1-oxyl, 4-hydroxy-2,2,6,6-tetramethylpiperidine-1-oxyl, 4-benzoyloxy-2,2,6,6-tetramethylpiperidine-1-oxyl, 4-methoxy-2,2,6,6-tetramethylpiperidine-1-oxyl and 4-oxtho-2,2,6,6-tetramethylpiperidine-1-oxyl. Among them, 2,2,6,6-tetramethylpiperidine-1-oxyl or 4-acethylamino-2,2,6,6-tetramethylpiperidine-1-oxyl is preferable.

Examples of the oxidantinclude sodium hypochlorite, bleaching powder or chlorine. Among them, sodium hypochlorite is preferable.

Chlorohydroxyaceton derivative obtained by the oxdation reaction can be purified according to general procedure. For example, 1-benzyloxy-3-chloro-2-propanon can be purified by extraction with an organic solvent such as ethyl acetate or toluene from the mixture, removing the solvent under reduced pressure, treating the same by carrying out distillation under reduced pressure or chromatography. Also, it can be employed in a subsequent step without such purification.

By the way, among the prepared chlorohydroxyacetone dervatives, the compound whose $R_2$ is benzyl group, that is 1-benzyloxy-3-chloro-2-propanon is a novel compound whose usefulness is found by the present inventor.

In the present invention, an optically active chloropropanediol derivative can be prepared by reducing the thus-obtained chlorohydroxyacetone derivative in the presence of enzyme source having an activity to reduce the same stereoselectively.

In the reduction process of the present invention, example of the enzyme source having an activity to reduce chlorohydroxyacetone derivative stereospecifically includes the enzyme source derived from microorganism belonging to Candida genus, Cryptococcus genus, Debaryomyces genus, Dekkera genus, Dipodascus genus, Galacctomyces genus, Geotrichum genus, Hansenula genus, Komagataella genus, Kluyveromyces genus, Pichia genus, Rhodotorula genus, Yarrowia genus, Sporidiobolus genus, Yamadazyma genus, Torulaspora genus, Torulopsis genus, Trichosporon genus, Alcaligenes genus, Rhodococcus genus, Micrococcus genus, Absidia genus, Acrotheca genus, Aspergillus genus, Chaetomidium genus, Gibberella genus, Mortierella genus or Eupenicillium genus.

Concretely, preferable example includes the enzyme source derived from a microorganism selected from the group consisting of *Candida galacta* species, *Candida arborea* species, *Candida catenulata* species, *Candida etchellsii* species, *Candida glabrata* species, *Candida gropengiesseri* species, *Candida guilliermondii* species, *Candida magnoliae* species, *Candida maltosa* species, *Candida parapsilosis* species, *Candida pararugosa* species, *Candida pinus* species, *Candida rugosa* species, *Candida sake* species, *Candida saitoana* species, *Candida sorbophila* species, *Candida tropicalis* species, *Cryptococcus humicolus* species, *Cryptococcus laurentii* species, *Cryptococcus terreus* species, *Debaryomyces hansenii* species, *Debaryomyces sp. H list et Guiel* species, *Debaryomyces robertsiae* species, *Debaryomyces castellii* species, *Debaryomyces psedopolymorphus* species, *Dekkera anomala* species, *Dipodascus armillariae* species, *Dipodascus ovetensis* species, *Galacctomyces reessii* species, *Geotrichum fermentans* species, *Geotrichum fragrans* species, *Hansenula polymorpha* DL1 species, *Komagataella pastoris* species, *Kluyveromyces thermotolerans* species, *Pichia membranaefaciens* species, *Pichia naganishii* species, *Rhodotorula glutinis* species, *Yarrowia lipolytica* species, *Sporidiobolus johnsonii* species, *Yamadazyma farinosa* species, *Torulaspora globosa* species, *Trichosporon aquatile* species, *Alcaligenes xylosaxidens* subsp. *denitrificans* species, *Rhodococcus erythropolis* species, *Rhodococcus equi* species, *Micrococcus luteus* species, *Absidia glauca* species, *Acrotheca cerophila* species, *Aspergillus japonicus* species, *Aspergillus parasiticus* species, *Aspergillus terreus* species, *Chaetomidium fimeti* species, *Gibberella fujikuroi* species, *Mortierella ramanniana* var. *angulispora* species and *Eupenicillium baarnense* species. More preferable example includes the enzyme source derived from *Candida magnoliae* IFO 0705.

The above-mentioned microorganism being the enzyme source may be either wild strain or variant. As the enzyme source, a microorganism which is derived by genetic procedure such as cell fusion or genetic manipulation can be used.

The microorganism producing the present enzyme can be obtained according to the method which comprises a step of isolating and/or purifying those enzymes to determine the complete or partial amino acid sequence thereof, a step of obtaining the DNA sequence encoding the enzyme according to the amino acid sequence, a step of introducing the DNA into other microorganisms to obtain a transformed microorganism, and a step of cultivating the transformed microorganism to obtain the present enzyme (WO 98/35025). Examples thereof include a transformed cell transformed by plasmid comprising DNA encoding the above carbonyl-reductase and DNA encoding an enzyme capable of regenerating coenzyme to which the enzyme depends. Preferably, examples are a transformed cell such that the enzyme capable of regenerating coenzyme is glucose dehydrogenase, a transformed cell such that the glucose dehydrogenase is derived from *Bacillus megaterium*, a transformed cell such that the plasmid is pNTS1G, a transformed cell such that the transformed cell is *Escherichia coli* and the like. Concretely, *E. coli* HB101 (pNTS1G) accession No. FERM-BP 5835 is more preferable.

The medium for the microorganism is not particularly limited as long as the microorganism is proliferated thereon. Examples thereof are a normal liquid medium containing sugar such as glucose or sucrose; alcohol such as ethanol or glycerol; fatty acid such as oleic acid or stearic acid and ester thereof; and oil such as rapeseed oil or soybean oil as carbon source, ammonium sulfate, sodium nitrate, peptone, Casamino acid, cone steep liquor, bran, yeast extract or the like as nitrogen source, magnesium sulfate, sodium chloride, calcium carbonate, dipotassium hydrogenphosphate, potassium dihydrogenphosphate as inorganic salt; and malt extract, meat extract or the like as other nutrients. The cultivation is carried out in aerobic condition, and generally the cultivation time is about 1 to 5 days, pH of the medium is 3 to 9, and the temperature of cultivation is 10 to 50° C.

The reduction process of the present invention is carried out by adding chlorohydroxyacetone derivative as the substrate, coenzyme NAD(P) and culture of the above-mentioned microorganism or treated product thereof to an appropriate solvent, stirring them with adjusting pH.

Though the reaction condition varies in accordance with the enzyme, microorganism or treated product employed and the concentration of the substrate, the concentration of substrate is usually about 0.1 to 90% by weight, preferably about 1 to 50% by weight, the proportion of coenzyme NAD(P) is 0.0001 to 1% by mole, preferably 0.001 to 0.1% by mole based on the substrate, the reaction temperature is 10 to 50° C., preferably 20 to 40° C. The reaction pH is 4 to 9, preferably 4 to 8. The reaction time is 1 to 120 hours, preferably 4 to 72 hours. The substrate can be added all at once or continuously. The reaction can be carried out batchwise or continuously. In addition, when whole cell is used in the reduction process as enzyme source, the coenzyme may not be added depending on the concentration of the substrate because a certain quantity of coenzyme is present in the whole cell.

Herein, "culture of microorganism" means culture solution containing whole cell or cultivated whole cell. "Treated product thereof" means, for example, crude extract, lyophilized microorganism, dried microorganism with acetone or ground product of such microorganism by friction. Furthermore, such treated product thereof may be enzyme itself or one obtained by fixing the whole cell as it is by known procedure. The fixation may be carried out in the manner known to a person skilled in the art, for example, cross-link method, physical adsorption method, calthration method.

The amount of costly coenzyme used in the reduction process of the present invention can be significantly reduced by using the common coenzyme NAD(P)H regenerating system jointly. The representative Example of the NAD(P)H regenerating system is the method in which glucose dehydrogenase is used coupled with glucose.

When reaction similar to the above is carried out by using culture of transformed microorganism obtained by introducing, to the host microorganism, a gene coding a reductase and a gene coding an enzyme capable of regenerating coenzyme to which the enzyme depends, or by using a treated product thereof, an optically active chloropronediol derivative can be prepared at a lower cost since it is not necessary to prepare enzyme source necessary for regenerating coenzyme separately.

It is possible to purify the optically active chloropronediol derivative generated by reduction reaction according to general procedure. For example, (S)-1-benzyloxy-3-chloro-2-propanol can be purified by removing suspended materials such as whole cell by means of treatment such as centrifugation or filtration, if necessary, in case of using a microorganism and the like, followed by extraction with an organic solvent such as ethyl acetate or toluene from the mixture, then removing the solvent under reduced pressure, and treating the same by carrying out distillation under reduced pressure or chromatography.

Hereinafter, the present invention is explained in detail by means of Examples, but the present invention is not limited thereto.

EXAMPLE 1
1-benzyloxy-3-chloro-2-propanon

To the mixture consisting of 30 mmol (0.6 g) of 1-benzyloxy-3-chloro-2-propanol, 1.5 mmol (234 mg) of 2,2,6,6-tetramethylpiperidine-1-oxyl (TEMPO), 33 mmol (3.4 g) of sodium bromide, 90 mmol (7.50 g) of sodium hydrogencarbonate, 75 ml of ethyl acetate and 35 ml of water was added dropwise 47 mmol (32 g) of sodium hypochlorite aqueous solution (1.5 mmol/g) under cooling with ice. The temperature of the reaction system was about 4° C. and pH was about 8.5. After dropping was completed, stirring was further continued for 30 minutes. Thereto was added 20 ml of 5% aqueous solution of sodium thiosulfate and the organic layer was separated. The organic layer was dried over sodium sulfate, filtrated and concentrated under reduced pressure to obtain a crude product. 1-benzyloxy-3-chloro-2-propane in the amount of 4.5 g was obtained by purification with silica gel column. The yield was 75%.

$^1$H-NMR($\delta$, CDCl3) 4.21 (s, 2H), 4.28 (s, 2H), 4.57 (s, 2H), 7.3–7.4 (m, 5H).
$^{13}$C-NMR(d, CDCl$_3$) 46.7 (s), 73.6 (s), 73.7 (s), 128.0 (s), 128.3 (s), 128.6 (s), 136.6 (s), 200.2 (s, C=O).

EXAMPLE 2
1-benzyloxy-3-chloro-2-propanon

To the mixture consisting of 30 mmol (6.0 g) of 1-benzyloxy-3-chloro-2-propanol, 1.5 mmol (320 mg) of 4-acetylamino-2,2,6,6-tetramethylpiperidine-1-oxyl, 33 mmol (3.4 g) of sodium bromide, 90 mmol (7.50 g) of sodium hydrogencarbonate, 75 ml of ethyl acetate and 35 ml of water was added dropwise 47 mmol (32 g) of sodium hypochlorite aqueous solution (1.5 mmol/g) under cooling with ice. Temperature of the reaction system was about 4° C. and pH was about 8.5. After the dropping was completed, stirring was further continued for 30 minute. Thereto was added 20 ml of a 5% sodium thiosulfate aqueous solution and the organic layer was separated. The organic layer was dried over sodium sulfate, filtered off and concentrated under reduced pressure to obtain a crude product. It was purified with silica gel column to obtain 4 g of 1-chloro-3-benzyloxy-2-propanon. The yield was 67%.

EXAMPLE 3
1-chloro-3-phenyloxy-2-propanon

To the mixture consisting of 30 mmol (5.60 g) of 1-chloro-3-phenyloxy-2-propanol, 1.5 mmol (234 mg) of 2,2,6,6-tetramethylpiperidine-1-oxyl (TEMPO), 33 mmol (3.4 g) of sodium bromide, 90 mmol (7.50 g) of sodium hydrogencarbonate, 75 ml of ethyl acetate and 35 ml of water was added dropwise 47 mmol (32 g) of sodium hypochlorite aqueous solution (1.5 mmol/g) under cooling with ice. Temperature of the reaction system was about 4° C. and pH was about 8.5. After the dropping was completed, stirring was further continued for 30 minute. Thereto was added 20 ml of a 5% sodium thiosulfate aqueous solution and the organic layer was separated. The organic layer was dried over anhydrous sodium sulfate, filtered off and concentrated under reduced pressure to obtain a crude product. It was purified with silica gel column to obtain 4.51 g of 1-chloro-3-phenyloxy-2-propanon. The yield was 82%.

$^1$H-NMR($\delta$, CDCl$_3$) 4.43 (s, 2H), 4.77 (s, 2H), 6.90 (d, 1H), 7.01–7.05 (m, 2H), 7.26–7.34 (m, 2H).

EXAMPLE 4
1-chloro-3-toluensulfonyloxy-2-propanon

To the mixture consisting of 30 mmol (7.58 g) of 1-chloro-3-toluensulfonyloxy-2-propanol, 1.5 mmol (234 mg) of 2,2,6,6-tetramethylpiperidine-1-oxyl (TEMPO), 33 mmol (3.4 g) of sodium bromide, 90 mmol (7.50 g) of sodium hydrogencarbonate, 75 ml of ethyl acetate and 35 ml of water was added dropwise 47 mmol (32 g) of sodium hypochlorite aqueous solution (1.5 mmol/g) under cooling with ice. Temperature of the reaction system was about 4° C. and pH was about 8.5. After the dropping was completed, stirring was further continued for 30 minute. Thereto was added 20 ml of a 5% sodium thiosulfate aqueous solution and the organic layer was separated. The organic layer was dried over anhydrous sodium sulfate, and filtered off and concentrated under reduced pressure to obtain a crude product. It was purified with silica gel column to obtain 5.79 g of 1-chloro-3-toluensulfonyloxy-2-propanon. The yield was 77%.

$^1$H-NMR($\delta$, CDCl$_3$) 2.74 (s, 3H), 4.28 (s, 2H), 4.73 (s, 2H), 7.49 (d, 2H, J=8.3 Hz), 7.82 (d, 2H, J=8.3 Hz).

EXAMPLE 5
1-benzyloxy-3-chloro-2-propanon

To the mixture consisting of 30 mmol (6.44 g) of 1-benzoyloxy-3-chloro-2-propanol, 1.5 mmol (234 mg) of 2,2,6,6-tetramethylpiperidine-1-oxyl (TEMPO), 33 mmol (3.4 g) of sodium bromide, 90 mmol (7.50 g) of sodium hydrogencarbonate, 75 ml of ethyl acetate and 35 ml of water was added dropwise 45 mmol (30 g) of sodium hypochlorite aqueous solution (1.5 mmol/g) under cooling with ice. Temperature of the reaction system was about 4° C. and pH was about 8.5. After the dropping was completed, stirring was further continued for 30 minute. Thereto was added 20 ml of a 5% sodium thiosulfate aqueous solution and the organic layer was separated. The organic layer was dried over anhydrous sodium sulfate, filtered off and concentrated under reduced pressure to obtain a crude product. It was purified with silica gel column to obtain 5.56 g of 1-benzoyloxy-3-chloro-2-propanon. The yield was 87%.

$^1$H-NMR($\delta$, CDCl$_3$) 4.25 (s, 2H), 5.14 (s, 2H), 7.46–7.50 (m, 2H), 7.60–7.64 (m, 1H), 8.08–8.10 (m, 2H).

EXAMPLE 6
Optically Active-1-benzyloxy-3-chloro-2-propanol Yeast

Microorganisms as described below were inoculated on 5 ml of semisynthetic medium A (40 g of glucose, 3 g of yeast extract, 6.5 g of $(NH_4)_2HPO_4$, 1 g of $KH_2PO_4$, 0.8 g of $MgSO_4.7H_2O$, 0.06 g of $ZnSO_4.7H_2O$, 0.09 g of $FeSO_4.7H_2O$, 0.005 g of $CuSO_4.5H_2O$, 0.01 g of $MnSO_4.4H_2O$, 0.1 g of NaCl, 1 L of water, pH 7) which has been sterilized in a test tube, and cultivated with shaking at 30° C. for 2 or 3 days (seed culture).

The obtained seed in amount of 0.1 ml was inoculated on 5 ml of semisynthetic medium B (40 g of glucose, 3 g of yeast extract, 6.5 g of $(NH_4)_2HPO_4$, 1 g of $KH_2PO_4$, 0.8 g of $MgSO_4.7H_2O$, 0.06 g of $ZnSO_4.7H_2O$, 0.09 g of $FeSO_4.7H_2O$, 0.005 g of $CuSO_4.5H_2O$, 0.01 g of $MnSO_4.4H_2O$, 0.1 g of NaCl, 5 g of CaCO3, 3 drops of adecanol, 1 L of water) which has been sterilized in a test tube, and cultivated with shaking at 30° C. for 2 or 3 days.

After the cultivation, 1 ml of the medium adjusted to pH 5, 0.1 ml of 40% of glucose and 0.5 mg of 1-benzyloxy-3-chloro-2-propanone were mixed and shaken for a day at 30° C. After the reaction, the reaction mixture was extracted with an equal amount of acetic acid. The organic layer was diluted with acetonitrile up to 0.02%, and conversion ratio and stereoselectivity was determined using high pressure liquid chromatography. The results thereof are shown in Table 1.

TABLE 1

| Microorganism | Yeild (%) | Optical purity (% ee) | Configuration |
|---|---|---|---|
| Candida galacta IFO10031 | 69.7 | 89.9 | S |
| Candida arborea IAM4147 | 84.7 | 48.5 | S |
| Candida catenulata IFO0731 | 90.1 | 44.1 | S |
| Candida etchellsii IFO1942 | 42.8 | 96.5 | S |
| Candida glabrata IFO0005 | 55.9 | 43.5 | S |
| Candida gropengiesseri IFO0659 | 100.0 | 47.8 | S |
| Candida guilliermondii IFO0454 | 60.5 | 78.1 | S |
| Candida magnoliae IFO0705 | 100.0 | 88.7 | S |
| Candida parapsilosis IFO0585 | 70.3 | 80.5 | S |
| Candida pararugosa IFO0966 | 45.6 | 100.0 | S |
| Candida rugosa IFO1364 | 59.5 | 86.7 | S |
| Candida sorbophila IFO1583 | 57.1 | 86.5 | S |
| Candida tropicalis IFO0589 | 45.5 | 49.5 | S |
| Cryptococcus humicolus IFO0760 | 97.1 | 92.4 | S |
| Cryptococcus laurentii IFO0609 | 49.8 | 75.0 | S |
| Debaryomyces hansenii IFO0066 | 44.5 | 80.6 | S |
| Debaryomyces sp.H list et Guiel IFO0025 | 74.5 | 77.3 | S |
| Debaryomyces robertsiae IFO1277 | 85.3 | 80.5 | S |
| Debaryomyces castellii IFO1359 | 85.4 | 88.4 | S |
| Debaryomyces psedopolymorphus IFO1026 | 65.7 | 90.6 | S |
| Dekkera anomala IFO0627 | 91.2 | 75.8 | S |
| Dipodascus armillariae IFO0102 | 49.1 | 57.3 | S |
| Debaryomyces ovetensis IFO1201 | 49.7 | 75.4 | S |
| Galactomyces reessii CBS179.60 | 97.0 | 81.7 | S |
| Geotrichum fermentans CBS452.83 | 39.4 | 77.7 | S |
| Geotrichum fragrans CBS164.32 | 37.3 | 87.8 | S |
| Hansenula polymorpha DL1 AKU4752 | 58.6 | 59.0 | S |
| Komagataella pastoris IFO0948 | 39.4 | 78.3 | S |
| Kluyveromyces thermotolerans IFO0662 | 81.3 | 56.6 | S |
| Pichia membranaefaciens IFO0186 | 30.9 | 58.5 | S |
| Pichia naganishii IFO1670 | 93.6 | 91.7 | S |
| Rhodotorula glutinis IFO1099 | 25.8 | 51.5 | S |
| Yarrowia lipolytica IFO0746 | 86.4 | 80.4 | S |
| Sporidiobolus johnsonii IFO6903 | 24.3 | 74.8 | S |
| Yamadazyma farinosa IFO0193 | 33.8 | 74.2 | S |
| Candida maltosa IFO1977 | 40.6 | 20.9 | R |
| Candida pinus IFO0741 | 46.5 | 51.6 | R |
| Candida sake IFO1517 | 35.8 | 14.5 | R |
| Candida saitoana IFO0380 | 53.0 | 42.2 | R |
| Cryptococcus humicolus CBS2756 | 20.2 | 61.2 | R |
| Cryptococcus terreus IFO0727 | 54.5 | 24.7 | R |
| Torulaspora globosa IFO0016 | 76.7 | 41.3 | R |
| Trichosporon aquatile ATCC22310 | 81.5 | 54.0 | R |
| Yamadazyma farinosa IFO0602 | 67.5 | 65.3 | R |

HPLC Analysis Condition (Conversion Ratio)
Column: Finepak C18:5 (made by JAPAN SPECTROSCOPIC Co., LTD.)
Elutriant: acetonitrile/0.1% solution of phosphate acid= 30/70

Flow rate: 0.7 ml/min

Detection wave length: 210 nm

HPLC Analysis Condition (Optical Purity)
Column: Chiralcel AS (made by DAICEL CHEMICAL INDUSTRIES, LTD.)

Elutriant: hexane/isopropanol=98/2

Flow rate: 1 ml/min

Temperature: 40° C.

Detection wave length: 210 nm

Bacteria

Microorganisms as described below were inoculated on 5 ml of the semisynthetic medium C (10 g of meat extract, 10 g of polypeptone, 5 g of yeast extract, 3 g of NaCl and 1 L of water, pH 7) which has been sterilized in a test tube, and cultivated with shaking at 30° C. for 2 or 3 days.

After the cultivation, 3 ml of the culture solution was centrifuged and the obtained cells were suspended into 1 ml of 0.1 M phosphate buffer (pH 5) containing glucose in amount of 4%. Thereto was added 0.5 mg of 1-benzyloxy-3-chloro-2-poropanon, then the mixture was shaken at 30° C. for a day.

After the reaction, the conversion ratio and optical purity were determined in the same manner as described above. The results thereof are shown in Table 2.

TABLE 2

| Microorganism | Yeild (%) | Optical purity (% ee) | Configuration |
|---|---|---|---|
| Alcaligenes xylosaxidens subsp. denitrificans ATCC15173 | 35.4 | 75.4 | S |
| Rhodococcus erythropolis IAM1440 | 56.3 | 32.8 | S |
| Rhodococcus equi JCM3132 | 35.3 | 39.7 | S |
| Escherichia coli HB101 (pNTS1G) | 100.0 | 100.0 | S |
| Micrococcus luteus IFO13867 | 30.7 | 62.0 | R |

Fungi

Microorganisms as described below were inoculated on 5 ml of the semisynthetic medium D (50 g of glucose, 50 g of corn steep liquor and 1 L of water, pH 6) which has been sterilized in a test tube, and cultivated with shaking at 28° C. for 2 or 3 days.

After the cultivation, 3 ml of the culture solution was centrifuged and the obtained cells were suspended into 1 ml of 0.1 M phosphate buffer (pH 5) containing glucose in amount of 4%. Thereto was added 0.5 mg of 1-benzyloxy-3-chloro-2-poropanon, then it was shaken at 30° C. for a day.

After the reaction, the conversion ratio and optical purity were determined in the same manner as described above. The results thereof are shown in Table 3.

TABLE 3

| Microorganism | Yeild (%) | Optical purity (% ee) | Configuration |
|---|---|---|---|
| Absidia glauca HUT1013 | 22.5 | 100.0 | S |
| Acrotheca cerophila IFO6881 | 13.5 | 100.0 | S |
| Aspergillus japonicus IFO4062 | 19.0 | 100.0 | S |
| Aspergillus parasiticus IFO4301 | 17.1 | 100.0 | S |
| Aspergillus terreus IFO7078 | 19.3 | 56.0 | S |
| Chaetomidium fimeti IFO30419 | 33.5 | 80.1 | S |
| Gibberella fujikuroi IFO6603 | 28.5 | 87.6 | S |
| Mortierella ramanniana var. angulispora | 10.5 | 100.0 | S |

TABLE 3-continued

| Microorganism | Yeild (%) | Optical purity (% ee) | Configu- ration |
|---|---|---|---|
| IFO6744 | | | |
| *Eupenicillium baarnense* IFO6090 | 19.9 | 13.6 | R |

EXAMPLE 7

(S)-1-benzyloxy-3-chloro-2-propanol

A recombinant *E. coli* HB101 (pNTS1G) having accession No. FERM-BP 5835 was inoculated on 100 ml of the semisynthetic medium (15 g of glycerin, 3 g of yeast extract, 6 g of $Na_2HPO_4$, 3 g of $KH_2PO_4$, 2 g of NaCl, 0.5 g of $MgSO_4 \cdot 7H_2O$, 1 L of water, pH=7.2) which was sterilized in a 500 ml Sakaguchi flask, and cultivated with shaking at 37° C. for 28 hours. To 25 ml of the obtained culture solution were added 15.8 g of 55% glucose solution and 5.1 mg of NADP. Thereto was continuously added 5.3 g of 1-benzyloxy-3-chloro-2-propanon, and reaction was carried out for 5 hours with adjusting pH to 6.5 and stirring at 30° C. After the reaction, the reaction solution was extracted with ethyl acetate twice the amount and concentrated under reduced pressure to obtain a brown oily product. By purifying the product using silica gel column, a colorless and transparent oily product, (S)-benzyloxy-3-chloro-2-propanon was obtained (5.0 g; the yield was 94.4%). The optical purity was determined in the same manner as in Example 6 and it was 100% ee.

EXAMPLE 8

(S)-chloropropanediol Derivatives

The same reduction as in Example 7 was carried out using the compound of the formula (3) in which $R_2$ (or $R_3$ in case of the formula (5)) was phenyl group (Ph), tosyl group (Ts) or benzoyl group (Bz) as a substrate. To 1 ml of the medium used in Example 7 were added, 30 mg of chlorohydroxyacetone derivative, 50 mg of glucose and 1 mg of NADP. The mixture was shaken at 30° C., pH=6.5 for two hours. After the reaction, the reaction solution was extracted with acetic acid and concentrated under reduced pressure to obtain a corresponding (S)-chloropropanediol derivative. The product was analyzed using the HPLC (as in Example 6). The results thereof are shown in Table 4.

TABLE 4

| Substrate R= | Conversion % | Optical purity % ee | Configuration |
|---|---|---|---|
| Ph | 100 | 100 | S |
| Ts | 100 | 96.8 | S |
| Bz | 100 | 100 | S |

Industrial Applicability

According to the present invention, optically active chloropropanediol derivatives, especially (S)-1-benzyloxy-3-chloro-2-propanol, which are very useful as intermediates of medicinal products, can be efficiently prepared.

What is claimed is:

1. A process for preparing an optically active chioropropanediol derivative represented by the formula (4);

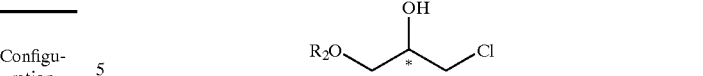

wherein $R_2$ is an alkyl group having 1 to 10 carbon atoms, an aryl group which may be substituted with a group having 1 to 15 carbon atoms, an aralkyl group which may be substituted with a group having 1 to 15 carbon atoms, an alkylsulfonyl group having 1 to 10 carbon atoms, an arylsulfonyl group which may be substituted with a group having 1 to 15 carbon atoms, an alkylcarbonyl group having 1 to 10 carbon atoms or an arylcarbonyl group which may be substituted with a group having 1 to 15 carbon atoms, which comprises allowing a chiorohydroxyacetone derivative represented by the formula (3);

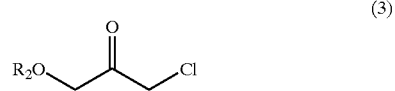

wherein $R_2$ is the same as the defined above, obtained by allowing the chloropropanediol derivative represented by the formula (2);

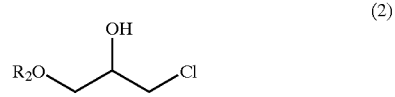

wherein $R_2$ is the same as the defined above, to react with a nitroxyl compound represented by the formula (7);

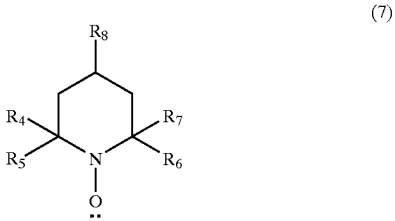

wherein each of $R_4$, $R_5$, $R_6$ and $R_7$ is an alkyl group which may be the same or different, $R_8$ is hydrogen atom or electron-releasing group, in the presence of an oxidizing agent, to be stereospecifically reduced in the presence of an enzyme source having an activity to reduce it stereospecifically.

2. The process for preparing an optically active chloropropanediol derivative of claim 1, wherein $R_2$ is t-butyl group, phenyl group, benzyl group, mesyl group, tosyl group, acetyl group or benzoyl group.

3. The process for preparing an optically active chloropropanediol derivative of claim 1, wherein the enzyme source is whole cell, culture of a microorganism belonging to Candida genus, Cryptococcus genus, Debaryomyces genus, Dekkera genus, Dipodascus genus, Galacctomyces genus, Geotrichum genus, Hansenula genus, Komagataella genus, Kluyveromyces genus, Pichia genus, Rhodotorula genus, Yarrowia genus, Sporidiobolus genus, Yamadazyma genus, Torulaspora genus, Torulopsis genus, Trichosporon genus, Alcaligenes genus, Rhodococcus genus, Micrococcus genus, Absidia genus, Acrotheca genus, Aspergillus genus, Chaetomidium genus, Gibberella genus, Mortierella genus or Eupenicillium genus, or a treated product thereof selected from the group consisting of crude extract, lyophilized microorganism, dried microorganism with acetone, and ground product of such microorganism by friction.

4. The process for preparing an optically active chloropropanediol derivative of claim 1, wherein the enzyme source is whole cell, culture of a microorganism selected from the group consisting of *Candida galacta* species, *Candida arborea* species, *Candida catenulata* species, *Candida etchellsii* species, *Candida glabrata* species, *Candida gropengiesseri* species, *Candida guilliermondii* species, *Candida magnoliae* species, *Candida maltosa* species, *Candida parapsilosis* species, *Candida pararugosa* species, *Candida pinus* species, *Candida rugosa* species, *Candida sake* species, *Candida saitoana* species, *Candida sorbophila* species, *Candida tropicalis* species, *Cryptococcus humicolus* species, *Cryptococcus laurentii* species, *Cryptococcus terreus* species, *Debaryomyces hansenii* species, Debaryomyces sp. H list et Guiel species, *Debaryomyces robertsiae* species, *Debaryomyces castellii* species, *Debaryomyces psedopolymorphus* species, *Dekkera anomala* species, *Dipodascus armillariae* species, *Dipodascus ovetensis* species, *Galacetomyces reessii* species, *Geotrichum fermentans* species, *Geotrichum fragrans* species, *Hansenula polymorpha* DL1 species, *Komagataella pastoris* species, *Kluyveromyces thermotolerans* species, *Pichia membranaefaciens* species, *Pichia naganishii* species, *Rhodotorula glutinis* species, *Yarrowia lipolytica* species, *Sporidiobolus johnsonii* species, *Yamadazyma farinosa* species, *Torulaspora globosa* species, *Trichosporon aquatile* species, *Alcaligenes xylosaxidens* subsp. *denitrificans* species, *Rhodococcus erythropolis* species, *Rhodococcus equi* species, *Micrococcus luteus* species, *Absidia glauca* species, *Acrotheca cerophila* species, *Aspergillus japonicus* species, *Aspergillus parasiticus* species, *Aspergillus terreus* species, *Chaetomidium fimeti* species, *Gibbrella fujikuroi* species, *Mortierella ramanniana* var. *angulispora* species and *Eupenicillium baarnense* species, or a treated product thereof selected from the group consisting of crude extract, lyophilized microorganism, dried microorganism with acetone, and ground product of such microorganism by friction.

5. The process for preparing an optically active chloropropanediol derivative of claim 1, wherein the enzyme source have an activity to reduce a chlorohydroxyacetone derivative represented by the formula (3) S-specifically.

6. The process for preparing an optically active chloropropanediol derivative of claim 5, wherein the enzyme source having a S-specific reducing activity is whole cell or culture of a microorganism belonging to Candida genus, Cryptococcus genus, Debaryomyces genus, Dekkera genus, Dipodascus genus, Galacctomyces genus, Geotrichum genus, Hansenula genus, Komagataella genus, Kluyveromyces genus, Pichia genus, Rhodotorula genus, Yarrowia genus, Sporidiobolus genus, Yamadazyma genus, Torulopsis genus, Alcaligenes genus, Rhodococcus genus, Micrococcus genus, Absidia genus, Acrotheca genus, Aspergillus genus, Chaetomidium genus, Gibberella genus or Mortierella genus, or a treated product thereof selected from the group consisting of crude extract, lyophilized microorganism, dried microorganism with acetone, and ground product of such microorganism by friction.

7. The process for preparing an optically active chloropropanediol derivative of claim 5, wherein the enzyme source having the S-specific reducing activity is whole cell or culture of a microorganism selected from the group consisting of *Candida galacta* species, *Candida arborea* species, *Candida catenulata* species, *Candida etchellsii* species, *Candida glabrata* species, *Candida gropengiesseri* species, *Candida guilliermondii* species, *Candida magnoliae* species, *Candida parapsilosis* species, *Candida pararugosa* species, *Candida rugosa* species, *Candida sorbophila* species, *Candida tropicalis* species, *Cryptococcus humicolus* species, *Cryptococcus terreus* species, *Debaryomyces hansenii* species, Debaryomyces sp. H. list et Guiel species, *Debaryomyces robertsiae* species, *Debaryomyces castellii* species, *Debaryomyces psedopolymorphus* species, *Dekkera anomala* species, *Dipodascus armillariae* species, *Dipodascus ovetensis* species, *Galacctomyces reessii* species, *Geotrichum fermentans* species, *Hansenula polymorpha* DL1 species, *Komagataella pastoris* species, *Kluyveromyces thermotolerans* species, *Pichia membranaefaciens* species, *Pichia naganishii* species, *Rhodotorula glutinis* species, *Yarrowia lipolytica* species, *Sporidiobolus johnsonii* species, *Yamadazyma farinosa* species, *Alcaligenes xylosaxidens* subsp. *denitrificans* species, *Rhodococcus erythropolis* species, *Rhodococcus equi* species, *Absidia glauca* species, *Acrotheca cerophila* species, *Aspergillus japonicus* species, *Aspergillus parasiticus* species, *Aspergillus terreus* species, *Chaetomidium fimeti* species, *Gibberella fujikuroi* species and *Mortierella ramanniana* var. *angulispora* species, or a treated product thereof selected from the group consisting of crude extract, lyophilized microorganism, dried microorganism with acetone, and ground product of such microorganism by friction.

8. The process for preparing an optically active chloropropanediol derivative of claim 5, wherein the enzyme source having the S-specific reducing activity is *Candida magnoliae* IFO 0705.

9. The process for preparing an optically active chloropropanediol derivative of claim 5, wherein the enzyme source having the S-specific reducing activity is a transformed cell with a plasmid comprising DNA encoding an carbonyl reductase derived from an microorganism belonging to Candida genus and DNA encoding an enzyme capable of regenerating coenzyme on which the reductase depends.

10. The process for preparing an optically active chloropropanediol derivative of claim 9, wherein the transformed cell is *E. coli* HB101 (pNTS1G) (accession No. FERM-BP 5835).

11. The process for preparing an optically active chloropropanediol derivative of claim 1, wherein the enzyme source have an activity to reduce chlorohydroxyacetone derivative represented by the formula (3) R-selectively.

12. The process for preparing an optically active chloropropanediol derivative of claim 11, wherein the enzyme source having R-specific reducing activity is whole cell or culture of a microorganism belonging to Candida genus, Cryptococcus genus, Torulaspora genus, Trichosporon genus, Yamadazyma genus, Micrococcus genus or Eupenicillium genus, or a treated product thereof selected from the group consisting of crude extract, lyophilized microorganism, dried microorganism with acetone, and ground product of such microorganism by friction.

13. The process for preparing an optically active chloropropanediol derivative of claim 11, wherein the enzyme source having R-specific reducing activity is whole cell or culture of a microorganism selected from the group consisting of *Candida maltosa* species, *Candida pinus* species, *Candida sake* species, *Candida saitoana* species, *Cryptococcus humicolus* species, *Cryptococcus terreus* species, *Torulaspora globosa* species, *Trichosporon aquatile* species, *Yamadazyma farinosa* species, or a treated product thereof selected from the group consisting of crude extract, lyophilized microorganism, dried microorganism with acetone, and ground product of such microorganism by friction.

14. A process for preparing an optically active chloropropanediol derivative represented by the formula (6):

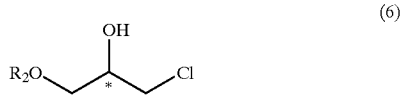

(6)

wherein $R_3$ is an alkyl group having 1 to 10 carbon atoms, an aryl group which may be substituted with a group having 1 to 15 carbon atoms, an aralkyl group which may be substituted with a group having 1 to 15 carbon atoms, an alkylsulfonyl group having 1 to 15 carbon atoms, an arylsulfonyl group which may be substituted with a group having 1 to 15 carbon atoms,
which comprises allowing a chlorohydroxyacetone derivative represented by the formula (5):

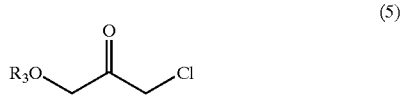

(5)

wherein $R_3$ is the same as the mentioned above, to be stereospecifically reduced in the presence of an enzyme source having an activity to reduce the chlorohydroxyacetone derivative represented by the above-mentioned formula (5) stereospecifically.

15. The process for preparing an optically active chloropropanediol derivative of claim 14, wherein $R_3$ is t-butyl group, phenyl group, benzyl group, mesyl group or tosyl group in the compound represented by the formula (5) or (6).

16. The process for preparing an optically active chloropropanediol derivative of claim 14, wherein the enzyme source having R-specific reducing activity is whole cell or culture of a microorganism belonging to Candida genus, Cryptococcus genus, Debaryomyces genus, Dekkera genus, Dipodascus genus, Galacctomyces genus, Geotrichum genus, Hansenula genus, Komagataella genus, Kluyveromyces genus, Pichia genus, Rhodotorula genus, Yarrowia genus, Sporidiobolus genus, Yamadazyma genus, Torulaspora genus, Torulopsis genus, Trichosporon genus, Alcaligenes genus, Rhodococcus genus, Micrococcus genus, Absidia genus, Acrotheca genus, Aspergillus genus, Chaetomidium genus, Gibberella genus, Mortierella genus, or Eupenicillium genus, or the treated product thereof selected from the group consisting of crude extract, lyophilized microorganism, dried microorganism with acetone, and ground product of such microorganism by friction.

17. The process for preparing an optically active chloropropanediol derivative of claim 14, wherein the enzyme source is whole cell or culture of a microorganism selected from the group consisting of Candida galacta species, Candida arborea species, Candida catenulata species, Candida etchellsii species, Candida glabrata species, Candida gropengiesseri species, Candida guilliermondii species, Candida magnoliae species, Candida maltosa species, Candida parapsilosis species, Candida pararugosa species, Candida pinus species, Candida rugosa species, Candida sake species, Candida saitoana species Candida sorbophila species, Candida tropicalis species, Cryptococcus humicolus species, Cryptococcus laurentii species, Cryptococcus terreus species, Debaryomyces hansenii species, Debaryomyces sp. list et Guiel species, Debaryomyces robertsiae species, Debaryomyces castellii species, Debaryomyces psedopolymorphus species, Dekkera anomala species, Dipodascus armillariae species, Dipodascus ovetensis species, Galacctomyces reessii species, Geotrichum fermentans species, Geotrichum fragrans species, Hansenula polymorpha DL1 species, Komagataella pastoris species, Kluyveromyces thermotolerans species, Pichia membranaefaciens species, Pichia naganishii species, Rhodotorula glutinis species, Yarrowia lipolytica species, Sporidiobolus johnsonii species, Yamadazyma farinosa species, Torulaspora globosa species, Trichosporon aquatile species, Alcaligenes xylosaxidens subsp. denitrificans species, Rhodococcus erythropolis species, Rhodococcus equi species, Micrococcus luteus species, Absidia glauca species, Acrotheca cerophila species, Aspergillus japonicus species, Aspergillus parasiticus species, Aspergillus terreus species, Chaetomidium fimeti species, Gibberella fujikuroi species, Mortierella ramanniana var. angulispora species and Eupenicillium baarnense species, or a treated product thereof selected from the group consisting of crude extract, lyophilized microorganism, dried microorganism with acetone, and ground product of such microorganism by friction.

18. The process for preparing an optically active chloropropanediol derivative of claim 14, wherein the enzyme source have an activity to reduce a chlorohydroxyacetone derivative represented by the formula (5) S-specifically.

19. The process for preparing an optically active chioropropanediol derivative of claim 18, wherein the enzyme source having the S-specific reducing activity is whole cell or culture of a microorganism belonging to Candida genus, Cryptococcus genus, Debaryomyces genus, Dekkera genus, Dipodascus genus, Galacctomyces genus, Geotrichum genus, Hansenula genus, Komagataella genus, Kluyveromyces genus, Pichia genus, Rhodotorula genus, Yarrowia genus, Sporidiobolus genus, Yamadazyma genus, Torulopsis genus, Alcaligenes genus, Rhodococcus genus, Micrococcus genus, Absidia genus, Acrotheca genus, Aspergillus genus, Chaetomidium genus, Gibberella genus or Mortierella genus, or a treated product thereof selected from the group consisting of crude extract, lyophilized microorganism, dried microorganism with acetone, and ground product of such microorganism by friction.

20. The process of preparing an optically active chloropropanediol derivative of claim wherein the enzyme source having the S-specific reducing activity is whole cell or culture of a microorganism selected from the group consisting of Candia galacta species, Candida arborea species, Candida catenulata species, Candida etchellsii species, Candida glabrata species, Candida gropengiesseri species, Candida guilliermondii species, Candida magnoliae species, Candida parapsilosis species, Candida pararugosa species, Candida rugosa species, Candida sorbophila species, Candida tropicalis species, Cryptococcus humicolus species, Cryptococcus terreus species, Debaryomyces hansenii species Debaryomyces sp. H list et Guiel species, Debaryomyces robertsiae species, Debaryomyces castellii species, Debaryomyces psedopolymorphus species, Dekkera anomala species, Dipodascus armillariae species, Dipodascus ovetensis species, Galacctomyces reessii species, Geotrichum fermentans species, Geotrichum fragrans species, Hansenula polymorpha DL1 species, Komagataella pastoris species, Kluyveromyces thermotolerans species, Pichia membranaefaciens species, Pichia naganishii species, Rhodotorula glutinis species, Yarrowia lipolytica species, Sporidiobolus johnsonii species, Yamadazyma farinosa species, Alcaligenes xylosaxidens subsp. denitrificans species, Rhodococcus erythropolis species, Rhodococcus equi species, Absidia glauca species, Acrotheca cerophila species, Aspergillus japonicus species, Aspergillus parasiticus species, Aspergillus terreus species, Chaetomidium

*fimeti* species, *Gibberella fujikuroi* species and *Mortierella ramanniana var. angulispora* species, or a treated product thereof selected from the group consisting of crude extract, lyophilized microorganism, dried microorganism with acetone, and ground product of such microorganism by friction.

21. The process for preparing an optically active chloropropanediol derivative of claim 18, wherein the enzyme source having the S-specific reducing activity is *Candida magnoliae* IFO 0705.

22. The process for preparing an optically active chloropropanediol derivative of claim 18, wherein the enzyme source having the S-specific reducing activity is a transformed cell with a plasmid comprising DNA encoding an carbonyl reductase derived from a microorganism belonging to Candida genus and DNA encoding an enzyme capable of regenerating coenzyme on which the reductase depends.

23. The process for preparing an optically active chloropropanediol derivative of claim 22, wherein the transformed cell is *E. coli* HB101 (pNTS1G) (accession No. FERM-BP 5835).

24. The process for preparing an optically active active chloropropanediol derivative of claim 14, wherein the enzyme source have an activity to reduce a chlorohydroxyacetone derivative represented by the formula (5) R-specifically.

25. The process for preparing an optically active chloropropanediol derivative of claim 24, wherein the enzyme source having R-specific reducing activity is whole cell or culture of a microorganism belonging to Candida genus, Cryptococcus genus, Torulaspora genus, Trichosporon genus, Yamadazyma genus, Micrococcus genus or Eupenicillium genus, or a treated product thereof selected from the group consisting of crude extract, lyophilized microorganism, dried microorganism with acetone, and ground product of such microorganism by friction.

26. The process for preparing an optically active chloropropanediol derivative of claim 24, wherein the enzyme source having R-specific reducing activity is whole cell or culture of a microorganism selected from the group consisting of *Candida maltosa* species, *Candida pinus* species, *Candida sake* species, *Candida saitoana* species, *Cryptococcus humicolus* species, *Cryptococcus terreus* species, *Torulaspora globosa* species, *Trichosporon aquatile* species, and *Yamadazyma farinosa* species, or the treated product thereof selected from the group consisting of crude extract, lyophilized microorganism, dried microorganism with acetone, and ground product of such microorganism by friction.

* * * * *

UNITED STATES PATENT AND TRADEMARK OFFICE
CERTIFICATE OF CORRECTION

PATENT NO. : 6,682,916 B2
DATED : January 27, 2004
INVENTOR(S) : Taoka et al.

It is certified that error appears in the above-identified patent and that said Letters Patent is hereby corrected as shown below:

Column 11,
Lines 66-67, change "chioropropanediol" to -- chloropropanediol --

Column 12,
Line 16, change "chiorohydroxyacetone" to -- chlorohydroxyacetone --

Column 13,
Lines 46-47, change "chioropropanediol" to -- chloropropanediol --

Column 15,
In formula 6, change "$R_2O$" to -- $R_3O$ --

Column 16,
Lines 24-25, change "chioropropanediol" to -- chloropropanediol --

Column 16,
Line 41, change "of claim wherein" to -- of claim 18 wherein --

Signed and Sealed this

First Day of June, 2004

JON W. DUDAS
*Acting Director of the United States Patent and Trademark Office*